(12) United States Patent
West et al.

(10) Patent No.: US 12,057,200 B1
(45) Date of Patent: Aug. 6, 2024

(54) SYNTHESIZER SYSTEM WITH INTERLEAVING VACUUM EXTRACTION

(71) Applicant: INTEGRATED DNA TECHNOLOGIES, INC., Skokie, IL (US)

(72) Inventors: Robert West, Solon, IA (US); Gregory Hodges, Coralville, IA (US)

(73) Assignee: INTEGRATED DNA TECHNOLOGIES, INC., Coralville, IA (US)

(*) Notice: Subject to any disclaimer, the term of this patent is extended or adjusted under 35 U.S.C. 154(b) by 1405 days.

(21) Appl. No.: 16/530,427

(22) Filed: Aug. 2, 2019

Related U.S. Application Data

(60) Provisional application No. 62/718,480, filed on Aug. 14, 2018.

(51) Int. Cl.
*G16C 20/60* (2019.01)
*C40B 50/04* (2006.01)
*G05B 19/05* (2006.01)
*G06F 9/54* (2006.01)
*B01J 19/00* (2006.01)
*B01L 3/00* (2006.01)

(52) U.S. Cl.
CPC ............. *G16C 20/60* (2019.02); *C40B 50/04* (2013.01); *G05B 19/05* (2013.01); *G06F 9/546* (2013.01); *B01J 19/0046* (2013.01); *B01J 2219/00324* (2013.01); *B01J 2219/00416* (2013.01); *B01J 2219/00686* (2013.01); *B01J 2219/00695* (2013.01); *B01L 3/50855* (2013.01); *B01L 2300/0893* (2013.01); *B01L 2400/049* (2013.01)

(58) Field of Classification Search
CPC ........ G16C 20/60; C40B 50/04; G05B 19/05; B01J 19/0046; B01J 2219/00324; B01J 2219/00416; B01J 2219/00686; B01J 2219/00695; B01L 3/50855; B01L 2300/0893; B01L 2400/049
See application file for complete search history.

(56) References Cited

U.S. PATENT DOCUMENTS 6,264,891 B1    7/2001  Heyneker et al.
11,738,345 B2 * 8/2023  Soto-Moreno .......... B01L 9/527
                                                   422/504

(Continued)

*Primary Examiner* — Shogo Sasaki
(74) *Attorney, Agent, or Firm* — Michael Best & Friedrich LLP

(57) ABSTRACT

Chemical synthesizer systems and methods for operating the same. One method includes receiving a first queue of instructions including a plurality of delivery instructions for operating a delivery assembly with respect to a plurality of synthesis plates and a plurality of vacuum instructions, grouped in a plurality of vacuum sections, for operating a vacuum assembly with respect to the plurality of synthesis plates. The method also includes sequentially processing each instruction included in the first queue of instructions by (i) executing the instruction when the instruction is one of the plurality of delivery instructions and (ii) moving, when the instruction is one of the plurality of vacuum instructions, one of the plurality of vacuum sections including the instruction to a second queue of instructions and executing instructions included in the second queue of instruction in parallel with instructions included in the first queue of instructions.

18 Claims, 11 Drawing Sheets

(56) References Cited

U.S. PATENT DOCUMENTS

| | | | |
|---|---|---|---|
| 2006/0127277 A1* | 6/2006 | Numajiri | G01N 35/08 |
| | | | 422/65 |
| 2007/0086923 A1* | 4/2007 | Li | B01L 3/0203 |
| | | | 422/400 |
| 2008/0177054 A1 | 7/2008 | Evans | |
| 2020/0316606 A1* | 10/2020 | Soto-Moreno | B01L 3/502792 |

* cited by examiner

FIG. 7

Plate A — 7.5 hour run on System X: V, D, V, D, V, D, V, D, V, D ...

Plate B — 7.5 hour run on System Y: V, D, V, D, V, D, V, D, V, D ...

| First Queue of Instructions | | |
|---|---|---|
| • turn_on | 1 | |
| • turn_on | 24 | |
| • turn_on | 22 | |
| • turn_on | 6 | |
| • turn_on | 7 | |
| • motor_move | 905 | |
| • motor_move_relative | 0 | |
| • turn_on_outputs | 10 | 33554430 |
| • wait | 280 | |
| • turn_off_outputs | 10 | 33554430 |
| • wait | 20 | |
| • motor_move_relative | 45 | |
| • turn_on_outputs | 10 | 33554430 |
| • wait | 280 | |
| • turn_off_outputs | 10 | 33554430 |
| • wait | 20 | |
| • Motor_move_relative | 45 | |
| • Turn_on_outputs | 10 | 33554430 |
| • Wait | 280 | |
| • Turn_off_outputs | 10 | 33554430 |
| • Wait | 20 | |
| • Motor_move_relative | 45 | |
| • Turn_on_outputs | 10 | 33554430 |
| • Wait | 280 | |
| • Turn_off_outputs | 10 | 33554430 |

| Second Queue of Instructions | |
|---|---|
| • vacuum_start | 2 |
| • turn_on | |
| • wait | |
| • turn_on | |
| • turn_on | |
| • turn_on | |
| • wait | |
| • turn_on | |
| • turn_on | |
| • wait | |
| • turn_off | |
| • turn_off | |
| • wait | |
| • turn_off | |
| • turn_off | |
| • turn_off | |
| • wait | |
| • turn_off | |
| • vacuum_end | 2 |

FIG. 10

SYNTHESIZER SYSTEM WITH INTERLEAVING VACUUM EXTRACTION

RELATED APPLICATIONS

This application claims priority to U.S. Provisional Application No. 62/718,480 filed on Aug. 14, 2018, the entire content of which is incorporated herein by reference.

FIELD

Embodiments described herein generally relate to chemical synthesizer systems and, in particular, synthesizer systems for interleaving vacuum instructions and delivery instructions to improve processing time for synthesizer systems including two synthesis plates.

SUMMARY

A chemical synthesizer system includes a synthesis plate with wells capable of holding a support for synthesis of a polymeric compound (membrane) or, alternatively, wells capable of holding a plurality of individual vials, wherein each vial has a dedicated well. Selected reagents are sequentially placed into the appropriate wells in a predetermined sequence. After reagents have been placed into a well for a predetermined amount of time, a vacuum extraction or flushing procedure is performed. During the vacuum extraction procedure, the reagents within an individual well are flushed and expelled. After the vacuum extraction procedure is complete, the well is ready to receive another reagent.

A controller, such as a programmable logic controller, controls the delivery and vacuuming of reagents from the wells. For example, high level instructions can be written that define when and how much of a reagent is to be delivered. These high level instructions are compiled into machine instructions that are loaded into the controller. The machine instructions define how the synthesis plate, the reagent delivery equipment, the vacuum equipment, or a combination thereof move to deliver and extract a particular reagent in a particular well.

The controller executes the machine instructions sequentially within a queue of instructions. In some embodiments, the controller is configured to, for each time slice, evaluate the current command in the queue and, if possible, process the next command in the queue as well. Thus, the controller may be configured to execute up to two commands per time slice.

Even with this processing efficiency, however, the machine instructions for processing one synthesis plate may include up to 400,000 instructions, which take approximately 7.5 hours to execute. If a synthesizer system includes two synthesis plates, the number of instructions needed to sequentially process these plates doubles to up to 800,000 and the processing time similarly doubles to approximately 15 hours.

Thus, embodiments described herein shorten the processing time for synthesizer systems that include a plurality of synthesis plates. In particular, as described in more detail below, machine instructions for processing the two (or more) plates are divided into vacuum instructions and delivery or main instructions, and the vacuum commands are copied (moved) to a separate instruction queue. Thus, during each time slice, the controller executes a vacuum command and a delivery command. Accordingly, the vacuum instructions are interleaved with the delivery instructions, which allows the vacuum assembly to be used to draw reagents through one or more wells of one plate at the same time as the delivery equipment is used to deliver reagents to one or more wells of the other plate. Thus, interleaving instructions, as described herein, reduces the processing time associated with processing two synthesis plates in a synthesizer system. For example, in some embodiments, interleaving instructions as described herein provides a processing rate approximately double a current rate for existing dual-plate synthesizer systems, which, in some situations, allows a synthesizer system to process two synthesis plates in about the same time currently required to process a single synthesis plate.

For example, one embodiment provides a chemical synthesizer system comprising a plurality of synthesis plates, a delivery assembly, a vacuum assembly, and a controller. Each of the plurality of synthesis plates includes a plurality of wells. The delivery assembly delivers a reagent to the plurality of wells included in each of the plurality of synthesis plates, and the vacuum assembly draws the reagent delivered by the delivery assembly through the plurality of wells included in each of the plurality of synthesis plates. The controller is configured to receive a first queue of instructions including a plurality of delivery instructions and a plurality of vacuum instructions. The plurality of delivery instructions are for operating the delivery assembly with respect to the plurality of synthesis plates, and a plurality of vacuum instructions are for operating the vacuum assembly with respect to the plurality of synthesis plates. The plurality of vacuum instructions are grouped in a plurality of vacuum sections. The controller is also configured to sequentially process each instruction included in the first queue of instructions. Sequentially processing each instruction included in the first queue of instructions includes (i) executing the instruction when the instruction is one of the plurality of delivery instructions, and (ii) moving one of the plurality of vacuum sections including the instruction to a second queue of instructions, when the instruction is one of the plurality of vacuum instructions, and executing instructions included in the second queue of instructions in parallel with instructions included in the first queue of instructions.

Another embodiment provides a method of operating a chemical synthesizer system the method includes receiving, with a controller, a first queue of instructions including a plurality of delivery instructions and a plurality of vacuum instructions. The plurality of delivery instructions are for operating a delivery assembly with respect to a plurality of synthesis plates, and the plurality of vacuum instructions are for operating a vacuum assembly with respect to the plurality of synthesis plates. The plurality of vacuum instructions are grouped in a plurality of vacuum sections. The method also includes sequentially processing, with the controller, each instruction included in the first queue of instructions. Sequentially processing each instruction included in the first queue of instructions includes (i) executing the instruction when the instruction is one of the plurality of delivery instructions, and (ii) moving one of the plurality of vacuum sections including the instruction to a second queue of instructions, when the instruction is one of the plurality of vacuum instructions, and executing instructions included in the second queue of instructions in parallel with instructions included in the first queue of instructions.

Yet another embodiment provides a non-transitory, computer-readable medium storing instructions that, when executed by at least one electronic processor, perform a set of functions. The set of functions including receiving a first queue of instructions including a plurality of delivery instructions and a plurality of vacuum instructions. The plurality of delivery instructions are for operating a delivery assembly with respect to a plurality of synthesis plates included in a chemical synthesizer system, and the plurality of vacuum instructions are for operating a vacuum assembly with respect to the first plate and the second plate. The plurality of vacuum instructions are grouped in a plurality of vacuum sections. The set of functions also including sequentially processing each instruction included in the first queue of instructions. Sequentially processing each instruction included in the first queue of instructions including (i) executing the instruction when the instruction is one of the plurality of delivery instructions, and, (ii) when the instruction is one of the plurality of vacuum instructions, moving one of the plurality of vacuum sections including the instruction to a second queue of instructions and executing instructions included in the second queue of instructions in parallel with instructions included in the first queue of instructions.

Other features and aspects of the invention will become apparent by consideration of the following detailed description and accompanying drawings.

BRIEF DESCRIPTION OF THE DRAWINGS

FIG. 7 illustrates delivery and vacuum sequences performed on two synthesis plates using two separate chemical synthesizer systems.

FIG. 10 illustrates an example first queue of instructions and an example second queue of instructions executed by a controller included in the chemical synthesizer system of FIG. 1 according to some embodiments.

DETAILED DESCRIPTION

One or more embodiments are described in the following description and illustrated in the accompanying drawings. These embodiments are not limited to the specific details provided herein and may be modified in various ways. Furthermore, other embodiments may exist that are not described herein. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way, but may also be configured in ways that are not listed. Furthermore, some embodiments described herein may include one or more electronic processors configured to perform the described functionality by executing instructions stored in non-transitory, computer-readable medium. Similarly, embodiments described herein may be implemented as non-transitory, computer-readable medium storing instructions executable by one or more electronic processors to perform the described functionality. As used in the present application, "non-transitory, computer-readable medium" comprises all computer-readable media but does not consist of a transitory, propagating signal. Accordingly, non-transitory computer-readable medium may include, for example, a hard disk, a CD-ROM, an optical storage device, a magnetic storage device, a ROM (Read Only Memory), a RAM (Random Access Memory), register memory, a processor cache, or any combination thereof.

In addition, the phraseology and terminology used herein is for the purpose of description and should not be regarded as limiting. For example, the use of "including," "containing," "comprising," "having," and variations thereof herein is meant to encompass the items listed thereafter and equivalents thereof as well as additional items. The terms "connected" and "coupled" are used broadly and encompass both direct and indirect connecting and coupling. Further, "connected" and "coupled" are not restricted to physical or mechanical connections or couplings and can include electrical connections or couplings, whether direct or indirect. In addition, electronic communications and notifications may be performed using wired connections, wireless connections, or a combination thereof and may be transmitted directly or through one or more intermediary devices over various types of networks, communication channels, and connections. Moreover, relational terms such as first and second, top and bottom, and the like may be used herein solely to distinguish one entity or action from another entity or action without necessarily requiring or implying any actual such relationship or order between such entities or actions.

Figure 1:
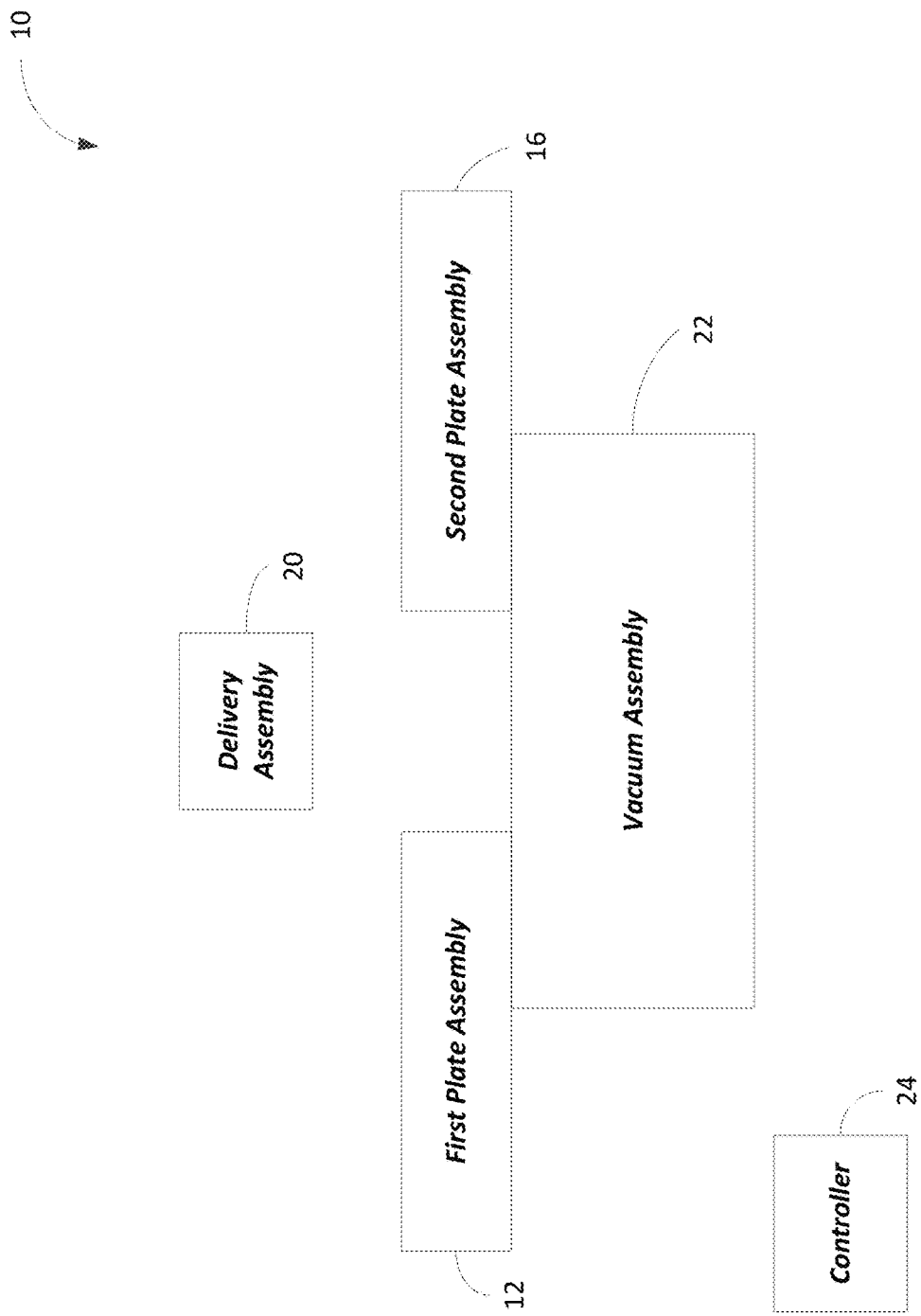
FIG. 1 schematically illustrates a chemical synthesizer system according to some embodiments.

FIG. 1 schematically illustrates a chemical synthesizer system 10. The system 10 may be used to synthesize oligonucleotides, as well as polymers such as peptides, polynucleotides, and other organic chains. As illustrated in FIG. 1, the system 10 includes a first plate assembly 12, a second plate assembly 16, a delivery assembly 20, a vacuum assembly 22, and a controller 24. It should be understood that the system 10 may include additional components than those illustrated in FIG. 1, and the components included in the system 10 may be arranged in various configurations. In the illustrated embodiment, the delivery assembly 20 is stationary, while the first plate assembly 12 and the second plate assembly 16 are movable (under control of the controller 24) underneath the delivery assembly 20. Thus, each plate assembly 12 and 16 may be associated with one or more actuators or motors (controlled via the controller 24) for independently moving one plate assembly with respect to the other plate assembly to position a plate in a desired positon with respect to the delivery assembly 20. It should be understood that, in other embodiments, the delivery assembly 20 is movable (via one or more actuators or motors) while the first plate assembly 12 and the second plate assembly 16 are stationary.

Figure 2:
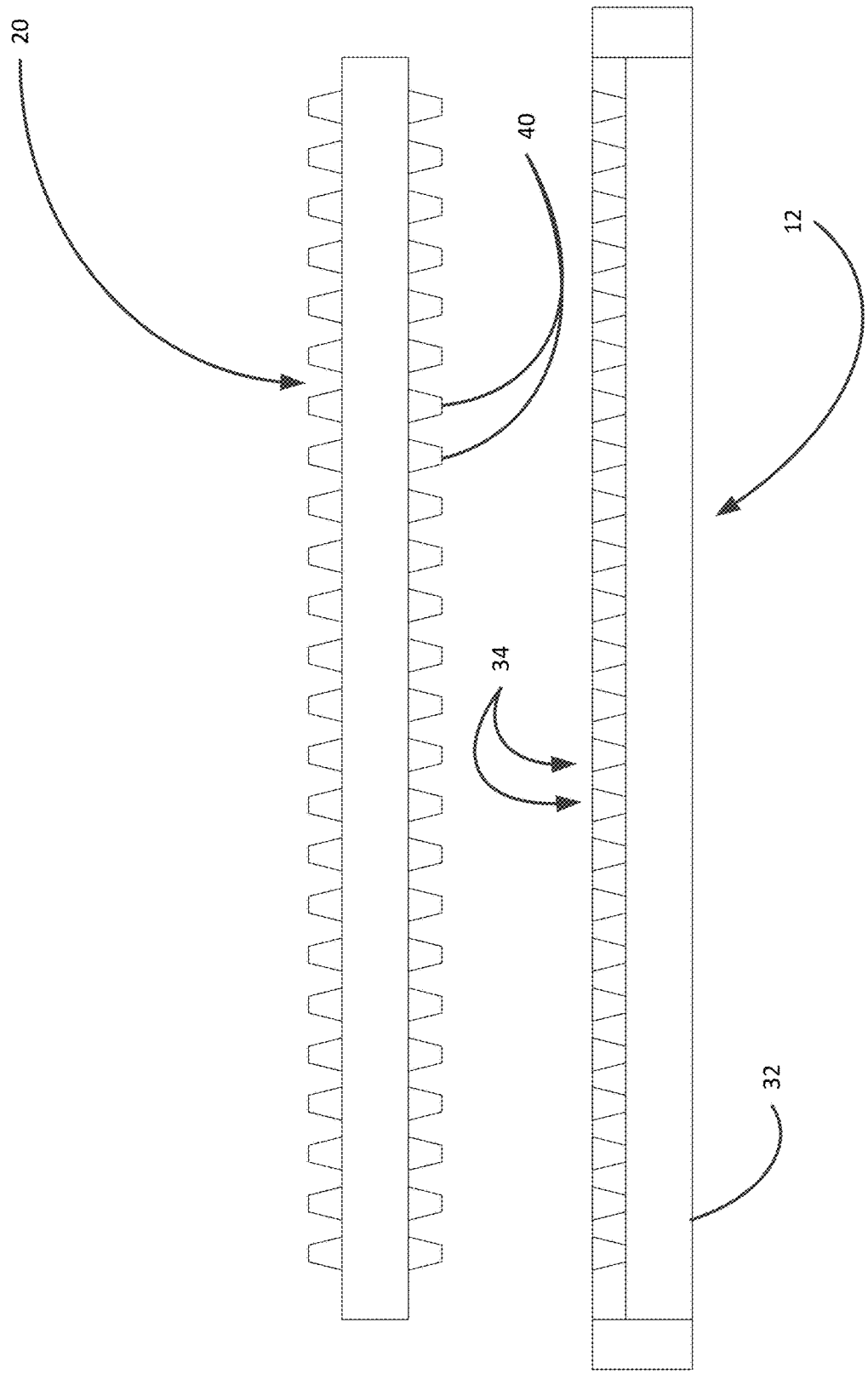
FIG. 2 is a perspective view of a plate assembly included in the chemical synthesizer system of FIG. 1 according to some embodiments.

FIG. 2 is a perspective view of the first plate assembly 12. As illustrated in FIG. 2, the first plate assembly 12 includes a synthesis plate 32 having a plurality of wells 34, which may be arranged in rows or a matrix. In some embodiments, each of the plurality of wells 34 is shaped and sized to receive a polymer compound (for example, a membrane containing linkers and a first base or a universal linker system).

As also illustrated in FIG. 2, the delivery assembly 20 includes a plurality of nozzles 40. During operation, reagents are dispensed from the nozzles 40 into the wells 34. It should be understood that FIG. 2 provides one example of the first plate assembly 12 and, in other embodiments, the first plate assembly 12 includes different components than those illustrated in FIG. 2 in various configurations. It should also be understood that the second plate assembly 16 may include similar components and constructions as the first plate assembly 12 although the second plate assembly 16 is not illustrated in FIG. 2. For example, in some embodiments, the second plate assembly 16 also includes a synthesis plate 32 with a plurality of wells 34 shaped and sized to receive a membrane that receives reagents from at least one nozzle 40 of the delivery assembly 20.

In some embodiments, the vacuum assembly 22 includes a vacuum block that includes a plurality of stand pipe apertures that receive stand pipes (not shown). The stand pipe apertures are coupled to and in communication with connection channels that pass through the vacuum block. The stand pipe apertures extend above an upper surface of the vacuum block to separate air from liquid (for example, reagents) within an area above the upper surface. Valves included in the vacuum assembly 22 (not shown) and coupled to the vacuum block are opened and closed (via the controller 24) to control the extraction or flushing of reagents from the wells 34. For example, the controller 24 may control one or more valves included in the vacuum assembly 22 to move air through the stand pipes to generate a vacuum pressure above the vacuum block, which draws reagents down through the stand pipe apertures along the upper surface of the vacuum block to a waste disposal. In some embodiments, each plate assembly 12 and 16 is positioned above the upper surface of a dedicated vacuum block, and each vacuum block may be associated with a dedicated vacuum generator. The reagent drawn from the plate assemblies 12 and 16 may be collected in separate waste disposals or a common disposal. It should be understood that the above description is provided as one example of the vacuum assembly 22 and, in other embodiments, the vacuum assembly 22 includes other types or configurations of components.

The controller 24 may include a programmable logic controller (PLC) that communicates (over a wired connection, a wireless connection, or a combination thereof) with the delivery assembly 20, the vacuum assembly 22, and each of the plate assemblies 12 and 16 to control the operation of each component as described herein. For example, the controller 24 may be configured to control movement of the plate assemblies 12 and 16 with respect to the delivery assembly 20, control operation of the delivery assembly 20 to deliver reagent to the wells 34 included in the plate assemblies 12 and 16, and control operation of the vacuum equipment to draw reagents through the plate assemblies 12 and 16.

Figure 3:
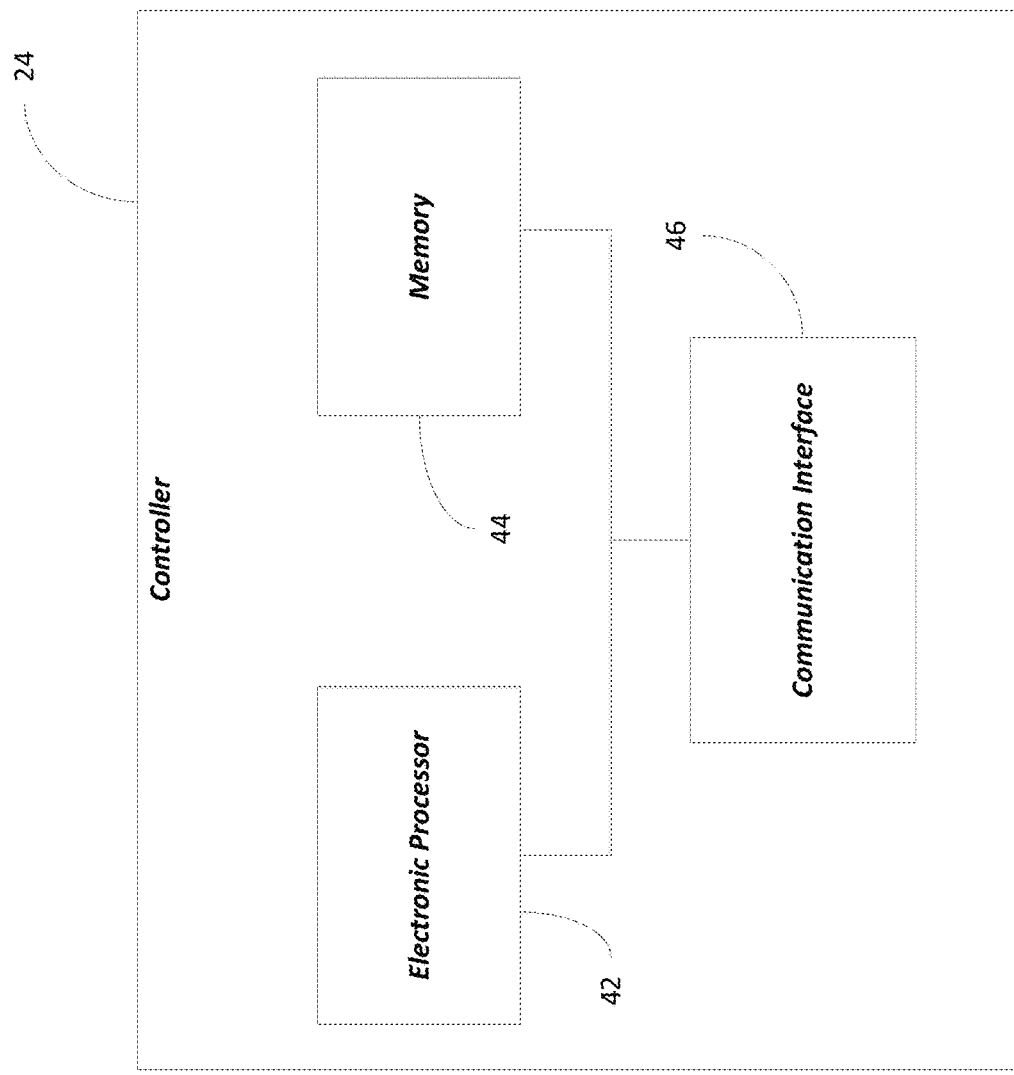
FIG. 3 schematically illustrates a controller included in the chemical synthesizer system of FIG. 1 according to some embodiments.

As illustrated in FIG. 3, in one embodiment, the controller 24 includes an electronic processor 42, a memory 44, and a communication interface 46. The electronic processor 42, the memory 44, and the communication interface 46 communicate wirelessly, over one or more wired communication channels or busses, or a combination thereof. The memory 44 includes non-transitory, computer-readable medium, such as random access memory, read-only memory, or a combination thereof. The electronic processor 42 can include a microprocessor configured to execute instructions stored in the memory 44. The memory 44 can also store data used with and generated by execution of the instructions. The communication interface 46 allows the controller 24 to communicate with other components of the system 10, including the delivery assembly 20, the vacuum assembly 22, the first plate assembly 12, and the second plate assembly 16. In some embodiments, the communication interface 46 also includes a wireless transceiver for communicating over a wireless communication network. It should be understood that the controller 24 may include additional components than those illustrated in FIG. 3 in various configurations. For example, in some embodiments, the controller 24 includes a plurality of electronic processors, a plurality of memories, a plurality of communication interfaces, or a combination thereof. Also, in some embodiments, the controller 24 may include one or more human machine interfaces (HMIs) for receiving input from a user, providing output to a user, or a combination thereof. In addition, it should be understood that the functionality described herein as being performed by the controller 24 may be distributed over multiple controllers included in the system 10.

Figure 4:
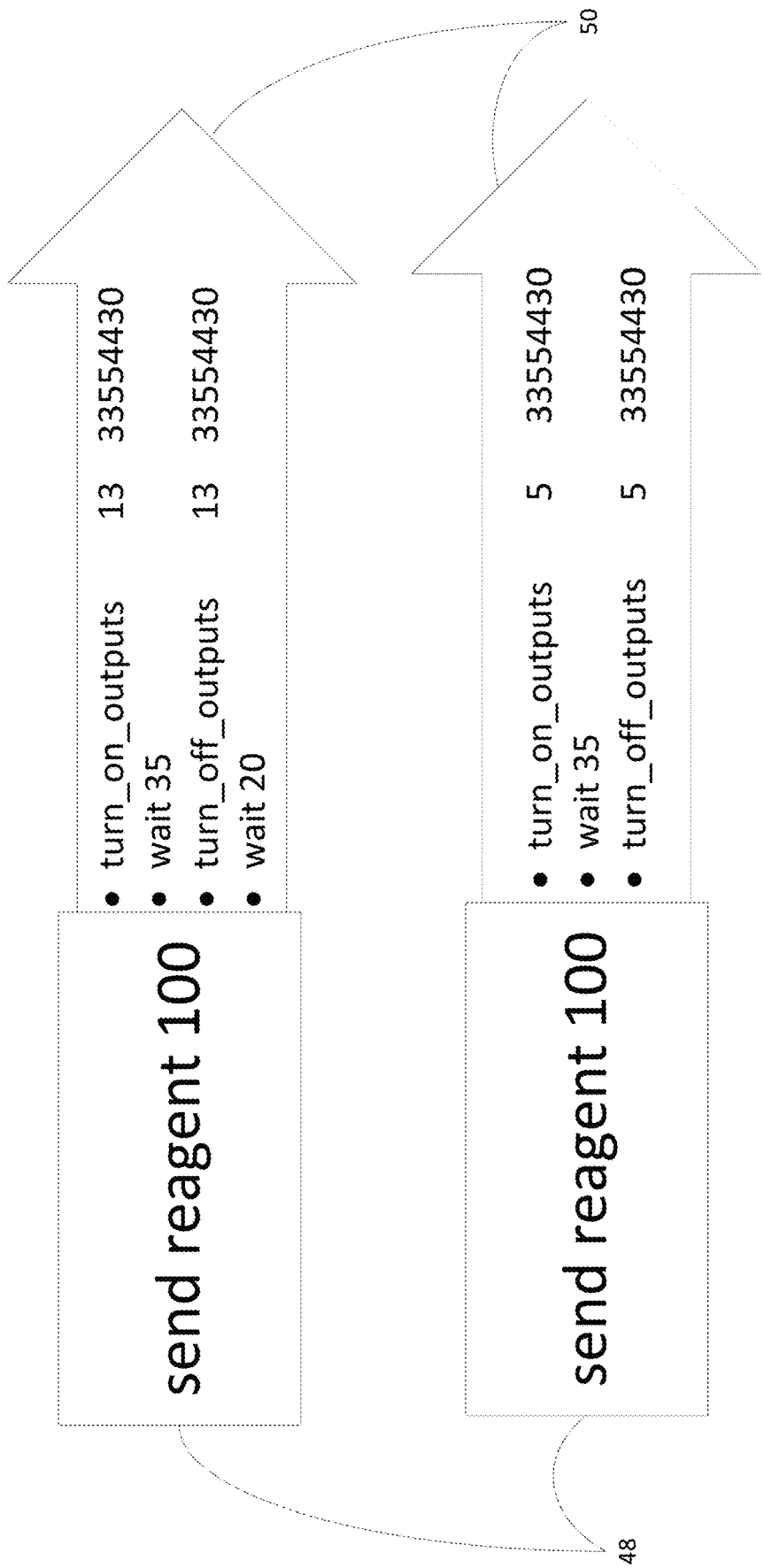
FIG. 4 illustrates translation of high level instructions for operating the chemical synthesizer system of FIG. 1 to machine instructions according to some embodiments.
Figure 5:
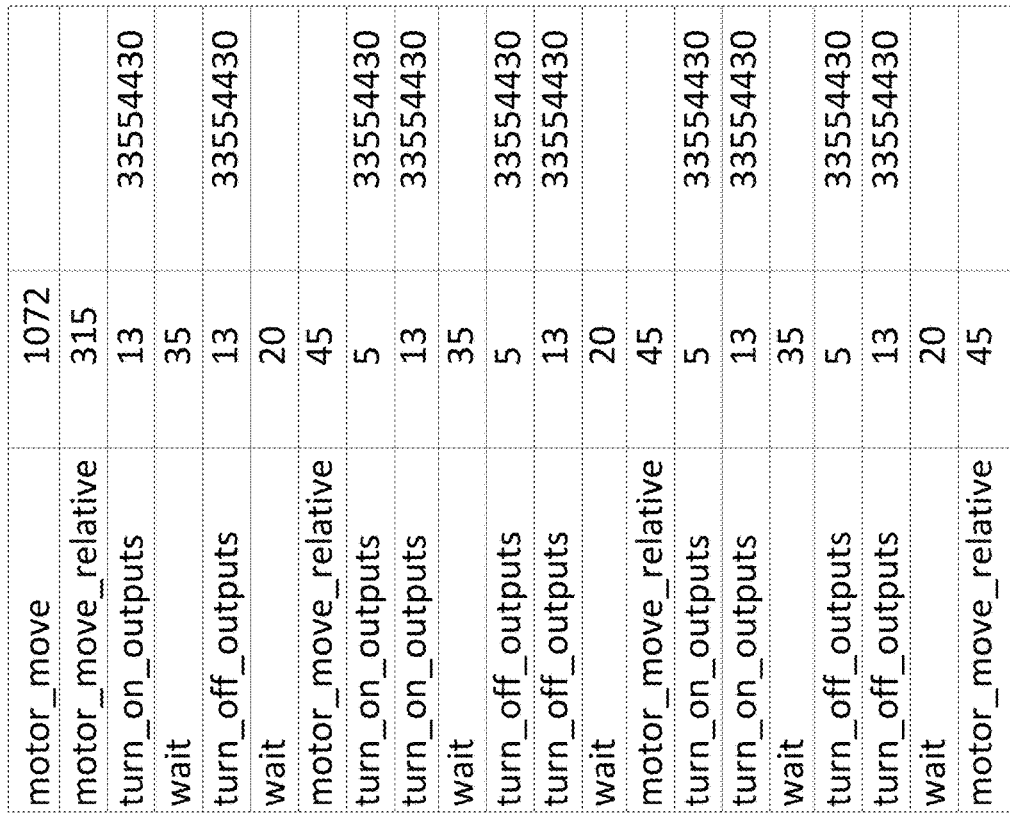
FIG. 5 illustrates example machine instructions for the chemical synthesizer system of FIG. 1 according to some embodiments.

As described above, the controller 24 executes machine instructions generated from high level instructions that define when and how much of a reagent is to be delivered. For example, FIG. 4 illustrates translation of high level instructions 48 ("send reagent 100" and "send reagent 100") to machine instructions 50. FIG. 5 also illustrates example machine instructions 52 generated from high level instructions. For each of the plate assemblies 12 and 16, the sequences defined by the high-level instructions are evaluated to create a set of machine instructions to implement the high-level instructions. In particular, the set of machine instructions move the plates 32 appropriate distances to align one or more wells 34 of the plates 32 with one or more nozzles 40 of the delivery assembly 20. For example, a plate 32 may be positioned so that each well 34 in one row of the plate 32 can receive reagents from the delivery assembly 20.

Figure 6:
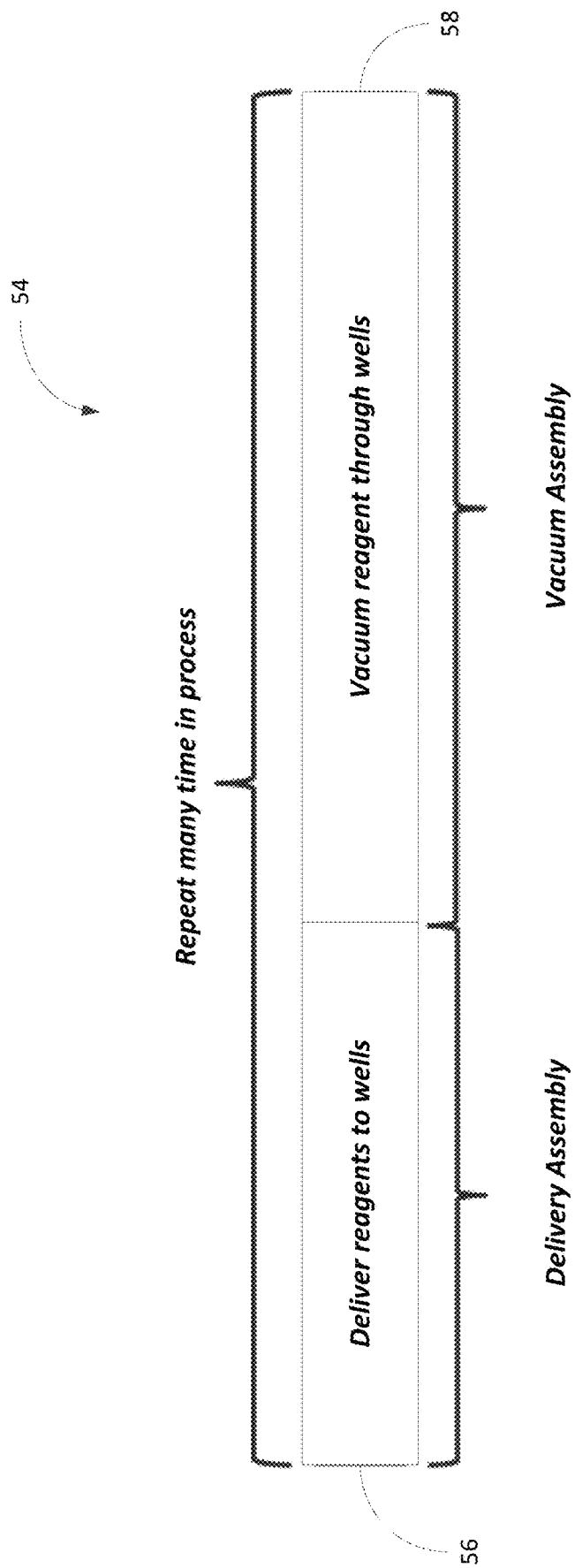
FIG. 6 illustrates a delivery and vacuum sequence performed using the chemical synthesizer system of FIG. 1 according to some embodiments.

As also discussed above, the controller 24 (the electronic processor 42) executes the machine instructions sequentially within a queue of instructions. The instructions include delivery instructions and vacuum instructions, wherein the delivery instructions control operation of the delivery assembly 20 and the plate assemblies 12 and 16 to deliver reagents to a plate 32 and the vacuum instructions control the vacuum assembly 22 to draw reagents through the wells 34 of a plate 32. For example, FIG. 6 represents a sequence 54 of delivering reagents to one or more wells 34 (a delivery step 56) and subsequently vacuuming reagent through the wells 34 (a vacuum step 58), wherein this sequence 54 is repeated multiple times to process a plate 32 (for example, for each row of wells 34 included in a plate 32). As illustrated in FIG. 6, in some embodiments, the amount of time associated with the delivery step 56 is less than the amount of time associated with the vacuum step 58.

Figure 8:
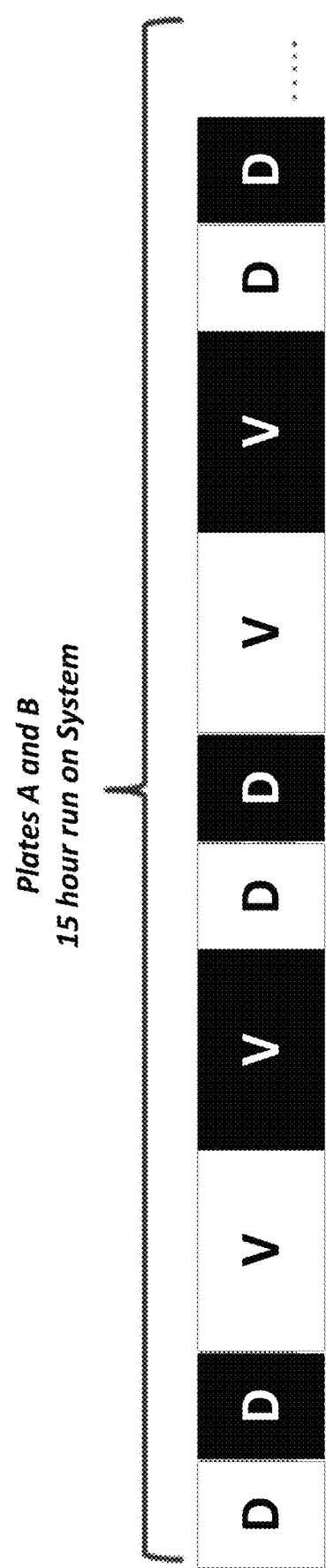
FIG. 8 illustrates delivery and vacuum sequences performed on two synthesis plates using a single chemical synthesizer system.

As illustrated in FIG. 7, when two plates (plates A and B) are processed on separate synthesizer systems (systems X and Y), each plate is processed by repeating the delivery and vacuum sequence 54 as represented in FIG. 6 on each system. As illustrated in FIG. 8, when a synthesizer system includes two plates (plates A and B), the machine instructions are traditionally structured such that the delivery assembly 20 is used to deliver reagents to one plate (plate A, delivery ("D") steps shown with white fill) and then the other plate (plate B, delivery ("D") steps shown with black fill), and, similarly, the vacuum assembly 22 is used to draw reagents through one plate (plate A, vacuum ("V") steps shown with white fill) and then the other plate (plate B, vacuum ("V") steps shown with black fill), wherein this sequential sequence is repeated multiple times. As illustrated in FIG. 8, this sequential processing of two plates within the same synthesizer system takes almost twice as long as when the plates are processed on separate systems.

Figure 9:
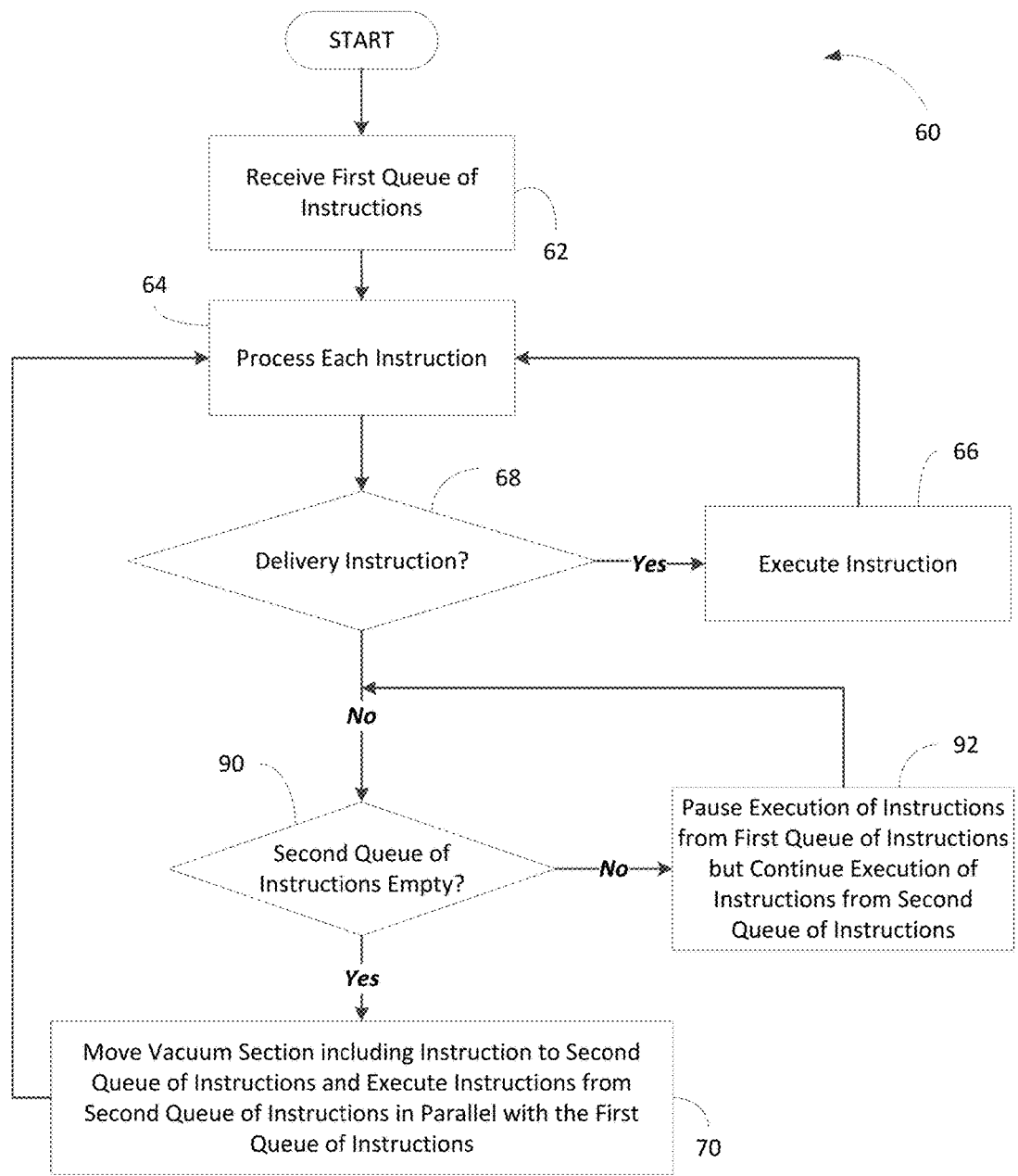
FIG. 9 is a flow chart illustrating a method of processing two synthesis plates using the chemical synthesizer system of FIG. 1 according to some embodiments.

Thus, to more efficiently operate a synthesizer system including two synthesis plates, the controller 24 is configured to interleave vacuum instructions with delivery instructions. For example, FIG. 9 illustrates a method 60 for interleaving vacuum instructions using the chemical synthesizer system 10. The method 60 is described as being performed by the controller 24 through execution of instructions by the electronic processor 42 (stored in the memory 44).

As illustrated in FIG. 9, the method 60 includes receiving, with the controller 24, a first or main queue of instructions ("first queue") (at block 62). As described above, the machine instructions included in the first queue of instructions are generated from the high level instructions and generally include a plurality of delivery instructions for operating the delivery assembly 20 with respect to the first plate assembly 12 and the second plate assembly 16 intermixed with a plurality of vacuum instructions for operating the vacuum assembly 22 with respect to the first plate assembly 12 and the second plate assembly 16. To identify the vacuum instructions within the first queue of instructions, high level commands can be used to mark or indicate a start of a sequence of vacuum instructions and an end of the sequence. For example, the high level command "vacuum_start #" can be used to mark the start of a sequence of vacuum instructions, and the high level command "vacuum_end #" can be used to mark the end of the sequence (wherein "#" represents a plate position that is being vacuumed). Thus, these commands can be used to mark each continuous (without any intervening delivery instructions) sequence of one or more vacuum instructions within the high level instructions, which can be translated to the machine instructions to mark vacuum sections. It should be understood that the start and end commands described above may be defined as part of the high level instructions or may be added as part of converting the high level instructions to machine instructions. For example, when the high level instructions are compiled or translated to machine instructions, the start and end commands may be automatically added around continuous sequences of vacuum instructions to mark the vacuum sections. In some embodiments, the controller 24 may perform this action as part of pre-processing or configuring the system 10 for operation.

The controller 24 sequentially processes instructions included in the first queue of instructions (at block 64). As described above, in some embodiments, the controller 24 is configured to execute two instructions per time slice. Accordingly, the controller 24 can sequentially process instructions included in the first queue of instructions by processing instructions in the order specified by first queue of instructions wherein two instructions are processed per time slice.

As illustrated in FIG. 9, processing each instruction in the first queue of instruction includes executing the instruction (at block 66) when the instruction is a delivery instruction (at block 68). As described above, executing a delivery instruction can include moving the delivery assembly 20, the first plate assembly 12, the second plate assembly 16, or a combination thereof or operating the delivery assembly 20 to deliver a reagent to a plate 32.

Alternatively, when the instruction is a vacuum instruction (at block 68), the controller 24 processes the instruction by copying the vacuum section including the vacuum instruction to a second queue of instructions ("second queue"), wherein instructions included in the second queue are processed sequentially in parallel with instructions included in the first queue (at block 70). As noted above, the controller 24 may be configured to execute two instructions per time slice. Thus, parallel processing of the instructions from the first and second queue of instructions may include processing one instruction from the first queue and one instruction from the second queue per time slice. When all of the instructions in the second queue have been executed (the second queue is empty) but the first queue still includes instructions needing execution, the controller 24 returns sequentially processing instructions in the first queue as described above (see blocks 66-70). Similarly, when all of the instructions in the first queue have been executed (the first queue is empty) but the second queue still includes instructions needing execution, the controller 24 executes instructions from the second queue. In this situation, the controller 24 may execute two instructions from the second queue per time slice since the first queue no longer includes instructions. After the controller 24 has executed all instructions from the first queue and the second queue, the method 60 ends and processing of the two plates 32 is complete.

For example, since vacuuming is not needed until after reagents have been delivered, the first queue of instruction likely starts with a set of delivery instructions. Thus, the controller 24 sequentially processes these instructions (for example, two instructions per time slice) until a vacuum instruction is encountered. When the controller 24 encounters a vacuum start command in the first queue (which may be during the same time slice as a delivery instruction is being executed), the controller 24 copies (moves) the vacuum section (marked by the start and end commands) from the first queue to the second queue. FIG. 10 illustrates an example first queue 80 and an example second queue 82, wherein the second queue 82 includes a vacuum section moved from the first queue 80.

Figure 11:
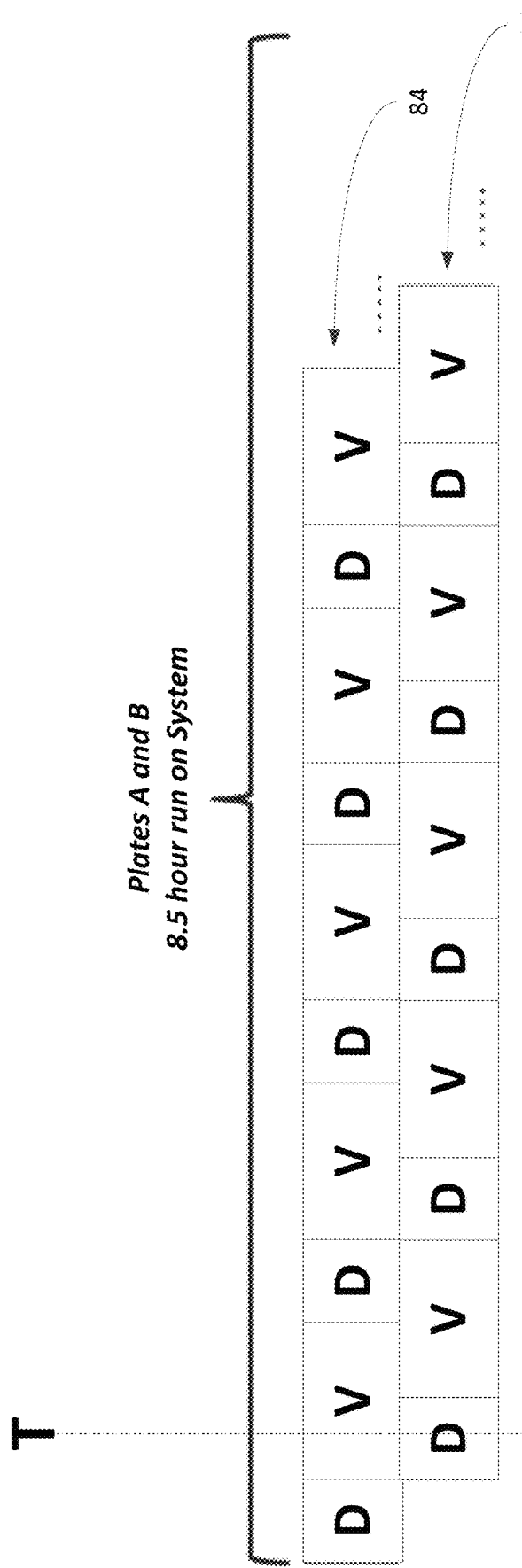
FIG. 11 illustrates interleaving delivery and vacuum sequences performed using the chemical synthesizer system of FIG. 1 as part of the method of FIG. 9 according to some embodiments.

As illustrated in FIG. 11, while the second queue includes instructions, an instruction from the first queue (a delivery instruction) can be executed within the same time slice as an instruction from the second queue (a vacuum instruction). Thus, the vacuum instructions interleave the delivery instructions to efficiently use the delivery assembly 20 and the vacuum assembly 22 to process the two plates 32. For example, as illustrated in FIG. 11, at time T, the vacuum assembly 22 is used to draw reagents through the first plate assembly 12 (plate A, delivery and vacuum steps shown in sequence 84) while at the same time the delivery assembly 20 is used to deliver reagents to the second plate assembly 16 (plate B, deliver and vacuum steps shown in sequence 86). As also illustrated in FIG. 11, interleaving the vacuum instructions with the delivery instructions reduces the total run time for executing the instructions for processing both plates 32 from 15 hours to approximately 8.5 hours. In other words, interleaving the vacuum instructions allows the chemical synthesizer system 10 to process two synthesis plates in about the same time as it takes to process one synthesis plate.

As illustrated in FIG. 9, in some embodiments, if the controller 24 reaches a vacuum instruction within the first queue (a vacuum section identified by a start command as described above) (at block 68) and the second queue still includes instructions needing execution (the second queue is not empty) (at block 90), the controller 24 pauses execution of instructions included in the first queue until all of the current vacuum instructions in the second queue are executed (at block 92). Accordingly, while the first queue of instructions is paused, the controller 24 continues to execute instructions from the second queue and, in some embodiments, may execute up to two instructions from the second queue per time slice. After the second queue is empty, the controller 24 copies the new vacuum section from the first queue to the second queue and executes instructions from both queues in parallel as described above.

Accordingly, embodiments described herein provide systems and methods for interleaving delivery instructions and vacuum instructions to efficiently process two synthesis plates included in a single synthesizer system. Interleaving the vacuum instructions with the delivery instructions reduces the time required to process the two synthesis plates such that two plates can be processed in approximately the same time as a single plate. It should be understood that the method and functionality described herein may be used with synthesizer systems that differ from the system 10 described herein. In particular, the functionality described herein can generally be applied to any synthesizer system including more than one synthesis plate.

Various features and advantages of some embodiments are set forth in the following claims.

What is claimed is:

1. A chemical synthesizer system comprising:
   a plurality of synthesis plates, each of the plurality of synthesis plates including a plurality of wells;
   a delivery assembly for delivering a reagent to the plurality of wells included in each of the plurality of synthesis plates;
   a vacuum assembly for drawing the reagent delivered by the delivery assembly through the plurality of wells included in each of the plurality of synthesis plates; and
   a controller, the controller configured to
      receive a first queue of instructions including a plurality of delivery instructions for operating the delivery assembly with respect to the plurality of synthesis plates and a plurality of vacuum instructions for operating the vacuum assembly with respect to the plurality of synthesis plates, the plurality of vacuum instructions grouped in a plurality of vacuum sections, and
      sequentially process each respective instruction included in the first queue of instructions by
         in response to the respective instruction being one of the plurality of delivery instructions, moving at least one of the plurality of synthesis plates or delivering regents to at least one of the plurality of synthesis plates by executing the respective instruction, and
         in response to the respective instruction being one of the plurality of vacuum instructions, moving one of the plurality of vacuum sections including the respective instruction to a second queue of instructions, and controlling at least one valve of the vacuum assembly by executing instructions included in the second queue of instructions in parallel with the sequential processing of instructions included in the first queue of instructions.

2. The system of claim 1, wherein the controller is further configured to sequentially process each respective instruction included in the first queue of instructions by processing two instructions from the first queue of instructions per time slice in response to the second queue of instructions not including any instructions.

3. The system of claim 1, wherein each of the plurality of vacuum sections includes a sequence of instructions from the plurality of vacuum instructions without any intervening instructions from the plurality of delivery instructions.

4. The system of claim 3, wherein a beginning of the sequence of instructions included in each of the plurality of vacuum sections is marked with a start command and an end of the sequence of instructions included in each of the plurality of vacuum sections is marked with an end command.

5. The system of claim 1, wherein the controller includes a programmable logic controller.

6. The system of claim 1, wherein each of the plurality of synthesis plates are moveable with respect to the delivery assembly.

7. The system of claim 1, wherein the controller is further configured to sequentially process each respective instruction included in the first queue of instructions by, in response to the respective instruction being one of the plurality of vacuum instructions and the second queue of instructions including instructions, pausing the sequential processing of instructions from the first queue of instructions while the second queue of instructions includes instructions.

8. The system of claim 7, wherein the controller is further configured to, while the sequential processing of instructions from the first queue of instructions is paused, execute up to two instructions from the second queue of instructions per time slice.

9. A method of operating a chemical synthesizer system, the method comprising:
   receiving, with a controller, a first queue of instructions including a plurality of delivery instructions for operating a delivery assembly with respect to a plurality of synthesis plates and a plurality of vacuum instructions for operating a vacuum assembly with respect to the plurality of synthesis plates, the plurality of vacuum instructions grouped in a plurality of vacuum sections; and
   sequentially processing, with the controller, each respective instruction included in the first queue of instructions by
      in response to the respective instruction being one of the plurality of delivery instructions, moving at least one of the plurality of synthesis plates or delivering regents to at least one of the plurality of synthesis plates by executing the respective instruction, and
      in response to the respective instruction being one of the plurality of vacuum instructions, moving one of the plurality of vacuum sections including the respective instruction to a second queue of instructions, and controlling at least one valve of the vacuum assembly by executing instructions included in the second queue of instructions in parallel with the sequential processing of instructions included in the first queue of instructions.

10. The method of claim 9, wherein sequentially processing each respective instruction included in the first queue of instructions further includes processing two instructions from the first queue of instructions per time slice in response to the second queue of instructions not including any instructions.

11. The method of claim 9, wherein moving the one of the plurality of vacuum sections to the second queue of instructions includes moving a sequence of instructions from the first queue of instructions, the sequence of instructions including one or more instructions included in the plurality of vacuum instructions without any intervening instructions included in the plurality of delivery instructions.

12. The method of claim 11, wherein moving the sequence of instructions includes moving instructions from the first queue of instructions marked with a start command and an end command.

13. The method of claim 9, wherein sequentially processing each respective instruction included in the first queue of instructions further includes, in response to the respective instruction being one of the plurality of vacuum instructions and the second queue of instructions including instructions, pausing the sequential processing of instructions from the first queue of instructions while the second queue of instructions includes instructions.

14. The method of claim 13, further comprising, while the sequential processing of instructions from the first queue of instructions is paused, executing up to two instructions from the second queue of instructions per time slice.

15. A non-transitory, computer-readable medium storing instructions that, when executed by at least one electronic processor, perform a set of functions, the set of functions comprising:
receiving a first queue of instructions including a plurality of delivery instructions for operating a delivery assembly with respect to a plurality of synthesis plates included in a chemical synthesizer system and a plurality of vacuum instructions for operating a vacuum assembly with respect to the plurality of synthesis plates, the plurality of vacuum instructions grouped in a plurality of vacuum sections; and
sequentially processing each respective instruction included in the first queue of instructions by
in response to the respective instruction being one of the plurality of delivery instructions, moving at least one of the plurality of synthesis plates or delivering regents to at least one of the plurality of synthesis plates by executing the respective instruction, and
in response to the respective instruction being one of the plurality of vacuum instructions, moving one of the plurality of vacuum sections including the respective instruction to a second queue of instructions, and controlling at least one valve of the vacuum assembly by executing instructions included in the second queue of instructions in parallel with the sequential processing of instructions included in the first queue of instructions.

16. The non-transitory, computer-readable medium of claim 15, wherein sequentially processing each respective instruction included in the first queue of instructions further includes processing two instructions from the first queue of instructions per time slice in response to the second queue of instructions not including any instructions.

17. The non-transitory, computer-readable medium of claim 15, wherein sequentially processing each respective instruction included in the first queue of instructions further includes, in response to the respective instruction being one of the plurality of vacuum instructions and the second queue of instructions including instructions, pausing the sequential processing of instructions from the first queue of instructions while the second queue of instructions includes instructions.

18. The non-transitory, computer-readable medium of claim 17, wherein the set of functions further comprises, while the sequential processing of instructions from the first queue of instructions is paused, executing up to two instructions from the second queue of instructions per time slice.

* * * * *